United States Patent
Agterberg et al.

(10) Patent No.: US 6,660,857 B2
(45) Date of Patent: Dec. 9, 2003

(54) PROCESS FOR THE PREPARATION OF ε-CAPROLACTAM

(75) Inventors: Frank P. W. Agterberg, Nieuwstadt (NL); Rudolf P. M. Guit, Maastricht (NL); Matthias R. J. Offermanns, Landgraaf (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/210,878

(22) Filed: Aug. 2, 2002

(65) Prior Publication Data

US 2003/0065169 A1 Apr. 3, 2003

Related U.S. Application Data

(63) Continuation of application No. PCT/NL01/00081, filed on Feb. 2, 2001.
(60) Provisional application No. 60/232,836, filed on Sep. 15, 2000.

(30) Foreign Application Priority Data

Feb. 3, 2000 (EP) ............................... 00200365

(51) Int. Cl.$^7$ ............................... C07D 201/08
(52) U.S. Cl. .................. 540/531; 540/538; 540/539
(58) Field of Search ............................ 540/531, 538, 540/539

(56) References Cited

U.S. PATENT DOCUMENTS

| 5,068,398 A | 11/1991 | Merger et al. ............... 560/156 |
|---|---|---|
| 5,495,014 A | 2/1996 | Fuchs et al. ................. 540/538 |
| 5,874,575 A | 2/1999 | Fuchs et al. ................. 540/539 |
| 5,877,314 A | 3/1999 | Herkes et al. ............... 540/538 |

FOREIGN PATENT DOCUMENTS

| EP | 729943 | 2/1996 |
| EP | 937712 | 2/1998 |
| WO | 97/30974 | 8/1997 |
| WO | 98/09944 | 3/1998 |
| WO | 98/37063 | 8/1998 |

OTHER PUBLICATIONS

Shleifman et al. (Vysokomolekulyarnye Soedineniya, Seriya A (1989), 31(10, 2089–94). Abstract.*

JP 45037773 (1970). Abstract.*

JP 45022946 (1970). Abstract.*

CA:1970:510328; Abstract of JP 45 022946.

* cited by examiner

Primary Examiner—Bruck Kifle
(74) Attorney, Agent, or Firm—Pillsbury Winthrop LLP

(57) ABSTRACT

A process for the preparation of ε-caprolactam starting from 6-aminocaproic acid, 6-aminocaproamide, 6-aminocaproic ester, 6-aminocapronitrile, oligomers or polymers of these compounds or mixtures comprising at least two of these compounds, which process is performed in the presence of N-(5-carboxypentyl)-ε-caprolactam and/or derivative thereof in an amount of less than 50 wt. % and more than 0.1 wt. % (based on the total reaction mixture).

19 Claims, No Drawings

PROCESS FOR THE PREPARATION OF ε-CAPROLACTAM

CROSS REFERENCE TO RELATED APPLICATION

This application is a continuation application based on International Application No. PCT/NL01/00081, filed Feb. 2, 2001, the disclosure of which in its entirety is incorporated herein by reference and claims the benefit of provisional application 60/232,836 filed Sep. 15, 2000.

The invention relates to a process for the preparation of ε-caprolactam starting from 6-aminocaproic acid, 6-aminocaproamide, 6-aminocaproic ester, 6-aminocapronitrile, oligomers or polymers of these compounds or mixtures comprising at least two of these compounds.

Such a process is described in JP-A-51039684. This patent publication describes a process to prepare ε-caprolactam from nylon-6 polymer using an adduct of ε-caprolactam and terephthalic acid, isophthalic acid or adipic acid as depolymerisation catalyst.

A disadvantage is that the catalyst is a process-foreign compound resulting in ε-caprolactam containing undesired impurities. Such impurities would not be present when the process is performed in the substantial absence of such process-foreign compounds.

The object of the present invention is a process for the preparation of ε-caprolactam in which the above mentioned disadvantage is avoided or at least reduced.

This object is achieved in that the process is performed in the presence of N-(5-carboxypentyl)-ε-caprolactam and/or derivative thereof in an amount of less than 50 wt. % and more than 0.1 wt. % (based on the total reaction mixture).

It has been found that the rate of the reaction of the process according to the invention is significantly higher than the rate of reaction of a process for the preparation of ε-caprolactam starting from the above mentioned compounds performed in the substantial absence of N-(5-carboxypentyl)-ε-caprolactam and/or derivative thereof or performed in the presence of higher amounts of N-(5-carboxypentyl)-ε-caprolactam and/or derivative thereof. This is advantageous because smaller reactor equipment can be used and/or less residence time is needed resulting in less degradation reactions. Degradation reactions result in yield loss and/or in the formation of undesirable by-products making the purification of ε-caprolactam more difficult. Another advantage is that N-(5-carboxypentyl)-ε-caprolactam and/or derivative thereof is a process-own compound so that the process of the invention does not result in ε-caprolactam containing extra impurities due to the use of a process-foreign catalyst compound.

JP-A-45022946 describes a process for the preparation of ε-caprolactam by reacting N-(5-carbamoylpentyl)-ε-caprolactam with aqueous ammonia at a temperature of 350° C. The compound N-(5-carboxypentyl)-ε-caprolactam itself is known from JP-A-45022946. The use of N-(5-carboxypentyl)-ε-caprolactam or derivative thereof as reaction rate enhancing compound in a process for preparing ε-caprolactam from 6-aminocaproic acid, 6-aminocaproamide, 6-aminocaproic ester, 6-aminocapronitrile, oligomers or polymers of these compounds or mixtures comprising at least two of these compounds is however not disclosed. N-(5-carboxypentyl)-ε-caprolactam is said to be obtained by processing the distillation residue that is obtained in the distillation of crude ε-caprolactam obtained by the reaction of caprolactone and aqeous ammonia. The N-(5-carboxypentyl)-ε-caprolactam must subsequently be converted into N-(5-carbamoylpentyl)-ε-caprolactam before the latter compound is reacted with aqueous ammonia at a temperature of 350° C. to obtain ε-caprolactam.

With N-(5-carboxypentyl)-ε-caprolactam is meant a compound with the following structural formula:

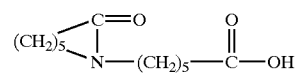

With N-(5-carbamoylpentyl)-ε-caprolactam is meant a compound with the following structural formula:

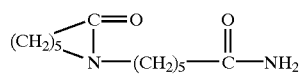

In the present application, the term N-(5-carboxypentyl)-ε-caprolactam derivative include compounds with the following structural formula:

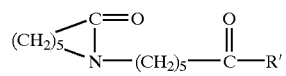

or with the following structural formula:

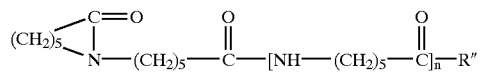

wherein R' is $NH_2$ or $OR^1$; n is at least 1; R" is OH, $NH_2$ or $OR^1$; $R^1$ is preferably an organic group with 1 to 20 carbon atoms and more preferably with 1 to 6 carbon atoms. The organic group is an alkyl, cycloalkyl, aryl or aralkyl group. More preferably $R^1$ is an alkyl group wit 1 to 6 carbon atoms. Examples of $R^1$ groups include methyl, ethyl, propyl, isopropyl, n-butyl, tert-butyl, isobutyl, cyclohexyl, benzyl and phenyl. By preference $R^1$ is methyl or ethyl.

The N-(5-carboxypentyl)-ε-caprolactam and N-(5-carbamoylpentyl)-ε-caprolactam can for example be prepared by the method as described in for example JP-A-45022946. The N-(5-carboxypentyl)-ε-caprolactam may be formed or can for example be prepared from di-(5-carboxypentyl)amine using the conditions as applied in the process of the invention according to the following reaction scheme:

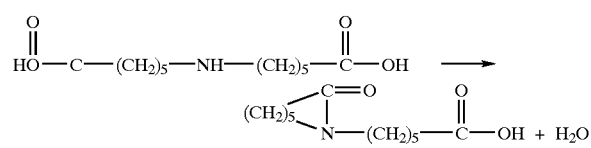

The di-(5-carboxypentyl)amine may be formed or can for example be prepared from 6-aminocaproic acid using the conditions as applied in the process of the invention according to the following reaction scheme:

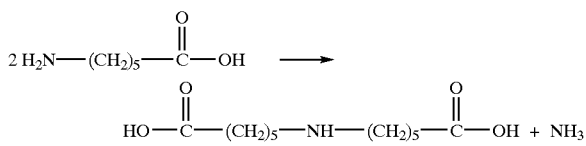

The di-(5-carboxypentyl)amine may be formed or can for example be prepared from 6-aminocaproic acid and a 5-formylvaleric acid ester using the conditions as described in for example WO-A-9835938 according to the following reaction scheme:

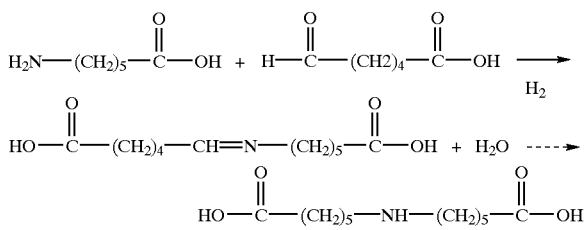

The compound with formula

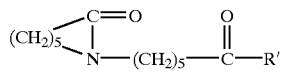

in which R' is as defined above, may be formed or can for example be prepared from 6-aminocaproic acid and 6-aminocaproamide (in case R' is —$NH_2$) or from 6-aminocaproic acid and 6-aminocaproate ester (in case R' is —$OR^1$) using the conditions as applied in the process of the invention.

In case the term N-(5-carboxypentyl)-ε-caprolactam is stated below, it should be read as N-(5-carboxypentyl)-ε-caprolactam and/or derivative thereof.

The N-(5-carboxypentyl)-ε-caprolactam may be added at the beginning of the process according to the present invention. The N-(5-carboxypentyl)-ε-caprolactam may also already be present in a reaction mixture obtained in a previous process step, which also contains at least one of 6-aminocaproic acid, 6-aminocaproamide, 6-aminocaproic ester, 6-aminocapronitrile, oligomers or polymers of these compounds.

Is has been found that the presence of N-(5-carboxypentyl)-ε-caprolactam in the reaction mixture in an amount of between 0.1 and 50 wt. % (based on the total reaction mixture) results in an increase of the reaction rate. With "the total reaction mixture" is meant the starting compound or mixture of starting compound (optionally containing water) which is fed to the process according to the invention. It has been found that the presence of N-(5-carboxypentyl)-ε-caprolactam in the reaction mixture in an amount higher than 50 wt. % results in a decrease of the reaction rate. The amount of N-(5-carboxypentyl)-ε-caprolactam in the reaction mixture is preferably between 0.1 wt. % and 10 wt. % (based on the total reaction mixture).

The amount of N-(5-carboxypentyl)-ε-caprolactam can also be kept at and/or brought to the desired value within the above general and preferred ranges by adding or by removing N-(5-carboxypentyl)-ε-caprolactam, for example by purging.

The process according to the invention may be performed in the gas phase by contacting the starting compound(s) (6-aminocaproic acid, 6-aminocaproamide, 6-aminocaproic ester, 6-aminocapronitrile, oligomers or polymers of these compounds or mixtures comprising at least two of these compounds) with superheated steam at a temperature of between 150 and 500° C. and a pressure of between 0.1 and 2 MPa.

An example of a possible gaseous phase process is described in WO-A-9837063. The process may also be performed in the liquid phase at elevated temperatures and super atmospheric pressures such as for example described in U.S. Pat. No. 4,730,040, EP-A-729944 and WO-A-9809944.

The process according to the invention is preferably performed in the gas phase. The gas phase processes are advantageous because ε-caprolactam is obtained in a gaseous steam phase in which no or partially no oligomers are present. This is advantageous because the purification of ε-caprolactam is easier. The gas phase is preferably performed as described in WO-A-9837063, the complete disclosure is incorporated herein as reference. The gas phase process is preferably performed at a temperature of between 250 and 400° C., more preferably at a temperature of between 270 and 350° C. Most preferably, the temperature is higher than 280° C. because higher selectivities to ε-caprolactam and thus a higher overall yield to ε-caprolactam is obtained. The pressure of the gas phase process is preferably between 0.5 and 2 MPa, more preferably below 1.5 MPa.

The starting mixture comprising 6-aminocaproic acid, 6-aminocaproate ester, 6-aminocaproamide, 6-aminocapronitrile, oligomers of these compounds and/or polymers of these compounds can be obtained by various processes. For example in U.S. Pat. No. 4,730,040 a process is described in which an aqueous mixture is obtained containing 6-aminocaproic acid and some ε-caprolactam starting from 5-formylvalerate ester. Further in EP-A-729943 a process is described in which an aqueous mixture is obtained containing 6-aminocaproic acid, 6-aminocaproamide and ε-caprolactam also starting from a 5-formylvalerate ester. U.S. Pat. No. 5,068,398 describes a process in which an aqueous mixture is obtained containing 6-aminocaproate ester and some ε-caprolactam starting from a 5-formylvalerate ester. WO-A-9835938 describes a process in which an aqueous mixture is obtained containing ε-caprolactam and 6-aminocaproic acid and/or 6-aminocaproamide starting from 5-formylvaleric acid or from an alkyl 5-formylvalerate in water.

The starting compounds are preferably 6-aminocaproic acid and/or 6-aminocaproamide because high yields to ε-caprolactam are possible when starting from these compounds. Next to the 6-aminocaproic acid and/or 6-aminocaproamide some ε-caprolactam and oligomers of ε-caprolactam, 6-aminocaproic acid and/or 6-aminocaproamide can be present. A typical mixture which can be used as starting mixture for the present invention comprises between 5 and 50 wt. % 6-aminocaproic acid, 10 and 50 wt. % 6-aminocaproamide, 0 and 40 wt. % ε-caprolactam and between 0 and 35 wt. % of the earlier mentioned oligomers in which the total of these fractions is 100 wt. %.

Starting mixtures can also be obtained starting from 6-aminocapronitrile as for example described in WO-A-9837063. Processes starting from 6-aminocapronitrile can yield mixtures comprising 6-aminocaproic acid. Such mixtures can be advantageously used in the process according to the invention. Firstly, the 6-aminocapronitrile is contacted with water under hydrolysis conditions. Secondly, water and ammonia, which is formed in the hydrolysis step, are preferably separated. In a third step the resulting mixture is treated with the process according to the invention.

The process according to the invention can also be applied on aqueous starting mixtures containing 6-aminocapronitrile. Processes to prepare ε-caprolactam starting from 6-aminocapronitrile are for example described in U.S. Pat. No. 5,495,016 and EP-A-659741.

Other examples of starting mixtures which can be used in the process according to the invention are polycaprolactam processing waste, polycaprolactam carpet waste and/or polycaprolactam extraction wash water.

When the process of the invention is performed in the gaseous phase, the starting compound or mixture of starting compounds are preferably contacted with the superheated steam as a liquid, for example as a melt. Polycaprolactam waste is preferably fed to the reactor as a melt. This feeding may be achieved by using an extruder, gear pump, or other means known in the art.

The process according to the present invention can be applied with particular advantage using an aqueous mixture obtained in a previous process step, which mixture already contains 6-aminocaproic acid, 6-aminocaproamide, 6-aminocaproic ester, 6-aminocapronitrile, oligomers and/or polymers of these compounds. The aqueous mixture contains between 1 and 50 wt. % water, preferably between 1 and 20 wt. % water and between 50 and 99 wt. % of starting compound(s), preferably between 80 and 99 wt. % of starting compounds. An aqueous mixture containing 6-aminocaproic acid, 6-aminocaproamide, oligomers thereof and ε-caprolactam can with particular advantage be obtained through reductive amination of 5-formylvaleric acid or its ester as for example described in EP-A-729934 or WO-A-9835938.

The 6-aminocaproic acid, 6-aminocaproamide and 6-aminocaproic ester compound respectively are of the following formula:

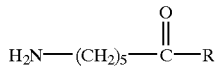

wherein R is OH, $NH_2$ and $OR^1$ respectively. $R^1$ is as defined above.

The 6-aminocapronitrile compound is of the following formula:

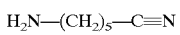

With the process according to the invention a composition is obtained comprising (a) ε-caprolactam and (b) N-(5-carboxypentyl)-ε-caprolactam, wherein the amount of component (b) in the composition is higher than 0.1 wt. % and lower than 50 wt % (based on the total composition).

The process according to the invention is preferably performed as a continuous process. The ε-caprolactam can be separated from the reaction mixture obtained in the process of the invention using any separation technique known to a person skilled in the art. Examples of suitable separation techniques are crystallisation, (vacuum) distillation and/or extraction.

In a preferred embodiment, the purification of ε-caprolactam comprises the following steps:
1) feeding the ε-caprolactam product stream obtained in the process according to the invention to a partial condensation unit in which the product stream is split into a top stream comprising steam and a liquid bottom stream comprising ε-caprolactam, water, lights and heavies;
2) feeding the liquid bottom stream to a distillation column of which the top stream is mainly water and the bottom stream comprises ε-caprolactam, lights and heavies;
3) feeding the latter bottom stream to a vacuum distillation column of which the top stream is mainly lights and the bottom stream comprises ε-caprolactam and heavies;
4) feeding the latter bottom stream to a vacuum distillation column of which the top stream is the ε-caprolactam stream and the bottom stream is the heavies stream.

Compounds having a higher boiling point than ε-caprolactam are designated as heavies in this specification. Examples are 6-aminocaproic acid, 6-aminocaproamide, oligomers of these compounds, and N-(5-carboxypentyl)-ε-caprolactam. Compounds having a lower boiling point than ε-caprolactam are designated as lights in this specification. Examples are N-methyl-ε-caprolactam, hexanoic acid, 5-hexenoic acid, valeric acid and valeramide.

The ε-caprolactam streams resulting from the process according to the invention can be purified according to conventional techniques. Advantageously the caprolactam is purified by a crystallisation process as for example described in WO-A-9948867.

The condensation of the product stream (step 1) is preferably performed at a temperature of 80–200° C., more preferably at a temperature of 100–170° C.

The distillation in step 2) is for example performed at a temperature of 60–160° C., preferably at a temperature of 80–140° C.

The distillation in step 3) and 4) is preferably performed at a pressure lower than 10 kPa, more preferably at a pressure lower than 5 kPa. The temperature of the distillation in step 3) and 4) is preferably between 110–170° C., more preferably between 120–150° C.

It has been found that N-(5-carboxypentyl)-ε-caprolactam has a beneficial effect on the rate of reaction for preparing ε-caprolactam from 6-aminocaproic acid, 6-aminocaproamide, 6-aminocaproic ester, 6-aminocapronitrile, oligomers or polymers of these compounds or mixtures comprising at least two of these compounds. The invention therefore also relates to the use of N-(5-carboxypentyl)-ε-caprolactam as reaction rate enhancing compound in a process for preparing ε-caprolactam from 6-aminocaproic acid, 6-aminocaproamide, 6-aminocaproic ester, 6-aminocapronitrile, oligomers or polymers of these compounds or mixtures comprising at least two of these compounds.

The invention also relates to a process for the preparation of polyamide-6 starting from water and 6-aminocaproic acid, 6-aminocaproamide, 6-aminocaproic ester, 6-aminocapronitrile, and/or ε-caprolactam which process in performed in the presence of N-(5-carboxypentyl)-ε-caprolacatam and/or derivative thereof in an amount of less than 50 wt % and more than 0.1 wt %. A process for the hydrolytic polymerisation of ε-caprolactam into polyamide-6 is for example described in *Kunststoff Handbuch* 3/4, Polyamide, Becker/Braun, Hanser Verlag, 1998, pages 41–47. A process for preparing polyamide-6 starting from 6-aminocapronitrile, and water is for example described in WO-A-9808889. It has been found that the presence of N-(5-carboxypentyl)-ε-caprolactam in such an amount has a beneficial effect on the rate of the hydrolytic polymerisation of 6-aminocaproic acid, 6-aminocaproamide, 6-aminocaproic ester, 6-aminocapronitrile and/or ε-caprolactam.

The invention will be elucidated by the following examples, however these are not intended to limit the scope of the invention in any way.

EXAMPLE I

A 500 ml autoclave having a turbine mixer was filled with 54 g 6-aminocaproic acid and 6.0 grams of N-(5-carboxypentyl)-ε-caprolactam. The autoclave was subsequently flushed with nitrogen and a pressure valve was adjusted such that the pressure in the reactor was maintained at 1.2 MPa. When the temperature reached 300° C., the substrate feed, consisting of an aqueous 14.5 wt % 6-aminocaproic acid solution, was started at a rate of 260 ml per hour. At the reaction conditions of 300° C. and 1.2 MPa the water in the feed is momentaneously converted into steam, which steam strips ε-caprolactam from the reaction melt.

After 1 hour a steady state was reached. The experiment was continued for another 7 hours at steady state conditions. The reactor contents at steady state conditions amounted to 50 grams of nylon-6-melt, containing 12 wt % N-(5-carboxypentyl)-ε-caprolactam. The steam containing ε-caprolactam leaving the reactor was condensed and analyzed. The accumulated condensed product, which was colourless on visual inspection, contained 254 grams of E-caprolactam, corresponding to 99% yield. Kinetics were fit using the Arrhenius equation, in which the activation energy was fixed and the rate constant $k_0$ calculated at $2.41 \times 10^5$ min$^{-1}$.

Comparative Experiment A

Example I was repeated without the addition of N-(5-carboxypentyl)-ε-caprolactam, keeping all other reaction conditions identical to example 1. At steady state, the reactor contained 67 grams of nylon-6 melt, and $k_0$ was calculated at $1.80 \times 10^5$ min$^{-1}$.

EXAMPLE 2

Example 1 was repeated, starting from a reductive amination mixture containing ε-caprolactam (33.9 wt %) and ε-caprolactam precursors (10.9 wt % 6-aminocaproic acid, 38.3 wt % 6-aminocapronamide, 13.6 wt % nylon-6 oligomers), as well as some N-(5-carboxypentyl)-ε-caprolactam (0.2 wt %) and water (3.1 wt %). Prior to reaction, 71 grams of the reductive amination mixture was charged to the reactor, and after flushing the autoclave with nitrogen and heating to 300° C. at 1.2 MPa pressure, the feed of an aqueous reductive amination mixture containing ε-caprolactam and ε-caprolactam precursors with a concentration corresponding to 14.5 wt % ε-caprolactam was started at a rate of 260 ml per hour.

Steady state conditions were reached after 1 hour. $k_0$ amounted to $1.85 \times 10^5$ min$^{-1}$ at this point, with 76 grams of nylon-6 melt in the reactor containing 0.2 wt. % N-(5-carboxypentyl)-ε-caprolactam.

After 29 hours running time, the feed rate was increased to 400 ml per hour. Reaction was continued for a total of 56 hours, after which the reactor contained 87 grams of nylon-6 melt in the new steady state, containing 5.3 wt. % N-(5-carboxypentyl)-ε-caprolactam. The reaction rate gradually increased during the course of the reaction; at t=56 hours, $k_0$ was calculated at $2.45 \times 10^5$ min$^{-1}$, showing a rate enhancement comparable to example 1. The accumulated condensed product contained 2600 grams of ε-caprolactam.

What is claimed is:

1. A process for the preparation of ε-caprolactam starting from 6-aminocaproic acid, 6-aminocaproamide, 6-aminocaproic ester, 6-aminocapronitrile, oligomers or polymers of these compounds or mixtures comprising at least two of these compounds, wherein the process is performed in the presence of N-(5-carboxypentyl)-ε-caprolactam and/or derivative thereof in an amount of less than 50 wt. % and more than 0.1 wt. % (based on the total reaction mixture), wherein said derivative has the structural formula

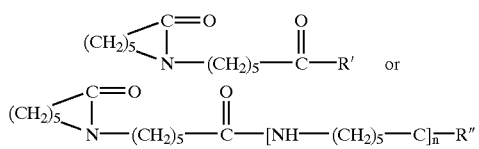

where R' is NH$_2$ or OR$^1$; n is at least 1; R" is OH, NH$_2$ or OR$^1$; and

R$^1$ is an organic group with 1 to 20 carbon atoms.

2. Process according to claim 1, wherein the starting mixture is an aqueous mixture containing 6-aminocaproic acid, 6-aminocaproamide, oligomers thereof and ε-caprolactam which aqueous mixture is obtained through reductive amination of 5-formylvaleric acid or its ester.

3. Process according to claim 1, wherein the starting mixture is an aqueous mixture containing 6-aminocapronitrile.

4. A method for enhancing the reaction rate for the conversion of 6-aminocaproic acid, 6-aminocaproamide, 6-aminocaproic ester, 6-aminocapronitrile, oligomers or polymers of these compounds or mixtures comprising at least two of these compounds to ε-caprolactam, which comprises carrying out the conversion reaction in the presence of a rate-enhancing effective amount of N-(5-carboxypentyl)-ε-caprolactam and/or derivative thereof wherein said derivative has the structural formula

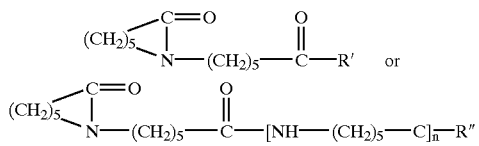

where R' is NH$_2$ or OR$^1$; n is at least 1; R" is OH, NH$_2$ or OR$^1$; and

R$^1$ is an organic group with 1 to 20 carbon atoms.

5. A composition comprising (a) ε-caprolactam and (b) N-(5-carboxypentyl)-ε-caprolactam, wherein the amount of component (b) in the composition is higher than 0.1 wt. % and lower than 50 wt % (based on the total composition).

6. A process for the preparation of polyamide-6 starting from water and 6-aminocaproic acid, 6-aminocaproamide, 6-aminocaproic ester, 6-aminocapronitrile and/or ε-caprolactam, wherein the process is performed in the presence of N-(5-carboxypentyl)-ε-caprolactam and/or derivative thereof in an amount of less than 50 wt % and more than 0.1 wt %, wherein said derivative has the structural formula

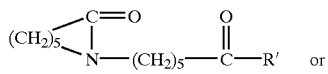

-continued

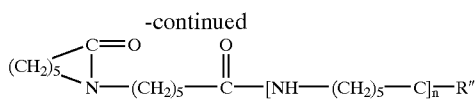

where R' is $NH_2$ or $OR^1$; n is at least 1; R" is OH, $NH_2$ or $OR^1$; and $R^1$ is an organic group with 1 to 20 carbon atoms.

7. A method for enhancing the reaction rate of a reaction mixture of water and ε-caprolactam, 6-aminocaproic acid, 6-aminocaproamide, 6-aminocaproic ester and/or 6-aminocapronitrile to prepare polyamide-6 which comprises adding a reaction-rate enhancing amount of N-(5-carboxypentyl)-ε-caprolactam and/or derivative thereof to the reaction mixture, wherein said derivative has the structural formula

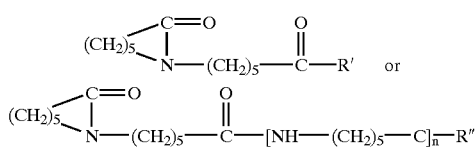

where R' is $NH_2$ or $OR^1$; n is at least 1; R" is OH, $NH_2$ or $OR^1$; and $R_1$ is an organic group with 1 to 20 carbon atoms.

8. Process according to claim 1, wherein the process is carried out in the presence of N-(5-carboxypentyl)-ε-caprolactam.

9. Process according to claim 1, wherein the amount of N-(5-carboxypentyl)-ε-caprolactam and/or said derivative thereof, is from 0.1 wt % to 10 wt %.

10. Process according to claim 1, which is performed in the presence of from 0.1 to 10 wt % of N-(5-carboxypentyl)-ε-caprolactam.

11. Process according to claim 1, which is carried out in the gas phase.

12. Process according to claim 1, wherein the starting mixture includes as reactants from 5 to 50 wt % 6-aminocaproic acid, from 10 to 50 wt % 6-aminocaproamide, 0 to 40 wt % ε-caprolactam 0 to 35 wt % oligomers of 6-aminocaproic acid and/or 6-aminocaproamide and/or ε-caprolactam, the total thereof being 100 wt %, and wherein the amount of N-(5-carboxypentyl)-ε-caprolactam and/or said derivative thereof, is from 0.1 wt % 10 wt %.

13. Composition according to claim 5, wherein the amount of component (b) is from 0.1 to 10 wt % based on the total composition.

14. Method according to claim 4, which comprises carrying out the conversion reaction in the presence of from 0.1 to 10 wt % of N-(5-carboxypentyl)-ε-caprolactam and/or said derivative thereof.

15. Method according to claim 4, which comprises carrying out the conversion reaction in the presence of from (0.1 to 10 wt % of N-(5-carboxypentyl)-ε-caprolactam.

16. Process according to claim 6, which comprises performing the process in the presence of from 0.1 to 10 wt % of N-(5-carboxypentyl)-ε-caprolactam and/or said derivative thereof.

17. Process according to claim 6, which comprises performing the process in the presence of from 0.1 to 10 wt % of N-(5-carboxypentyl)-ε-caprolactam.

18. Method according to claim 7, which comprises adding from 0.1 to 10 wt % of N-(5-carboxypentyl)-ε-caprolactam and/or said derivative thereof to the reaction mixture.

19. Method according to claim 7, which comprises adding from 0.1 to 10 wt % of N-(5-carboxypentyl)-ε-caprolactam to the reaction mixture.

\* \* \* \* \*